United States Patent [19]

Hogan et al.

[11] Patent Number: 5,356,374
[45] Date of Patent: Oct. 18, 1994

[54] PROCESS FOR TREATING BLOOD WITH POLYIMIDE CARRIERS

[75] Inventors: John J. Hogan; Alexander Kopatsis; Lorenzo F. Pelosi, all of Wilmington, Del.; Patrick T. Shannon, Drexel Hill, Pa.

[73] Assignee: E. I. du Pont de Nemours and Company, Wilmington, Del.

[21] Appl. No.: 935,349

[22] Filed: Aug. 28, 1992

Related U.S. Application Data

[63] Continuation of Ser. No. 491,585, Mar. 12, 1990, abandoned.

[51] Int. Cl.$^5$ ............................................. A61M 37/00
[52] U.S. Cl. .......................................... 604/4; 604/5; 604/6; 210/749; 210/195.2; 435/2
[58] Field of Search ................. 604/4, 5, 6; 210/749, 210/782, 787, 808, 195.2, 645, 679; 435/2

[56] References Cited

U.S. PATENT DOCUMENTS

| | | | |
|---|---|---|---|
| 2,999,788 | 9/1961 | Morgan | 162/146 |
| 3,179,634 | 5/1967 | Edwards | 260/78 |
| 3,901,808 | 8/1975 | Bokros | 604/4 |
| 4,362,155 | 12/1982 | Skurkovich | 128/214 R |
| 4,520,071 | 5/1985 | Noda et al. | 428/402 |
| 4,588,804 | 5/1986 | Fryd | 528/125 |
| 4,614,513 | 9/1986 | Bensinger | 604/6 |
| 4,619,639 | 10/1986 | Nosé et al. | 604/4 |
| 4,778,767 | 10/1988 | Hummelen et al | 435/180 |
| 4,895,558 | 1/1990 | Cham | 604/4 |
| 4,990,384 | 2/1991 | Jinbo | 428/357 |
| 5,133,703 | 7/1992 | Boehringer et al. | 604/4 |
| 5,211,850 | 5/1993 | Shettigar et al. | 604/5 |

FOREIGN PATENT DOCUMENTS

| | | | |
|---|---|---|---|
| 3523615 A1 | 1/1987 | Fed. Rep. of Germany | A61L 31/00 |
| WO86/03840 | 7/1986 | World Int. Prop. O. | G01N 33/545 |

*Primary Examiner*—Randall L. Green
*Assistant Examiner*—Prebilic: Paul

[57] ABSTRACT

The present invention relates to a process for treating blood. The process involves separating the blood into plasma and cellular components. The plasma component is passed through a column containing a polyimide particulate carrier. The polyimide carrier contains immobilized proteins, such as protein A, bonded to its surface. The polyimide carrier can be used for removing or modifying a biochemically active substance in the blood plasma.

3 Claims, 1 Drawing Sheet

PROCESS FOR TREATING BLOOD WITH POLYIMIDE CARRIERS

This is a continuation of application Ser. No. 07/491,585 filed Mar. 12, 1990, now abandoned.

BACKGROUND OF THE INVENTION

Biochemically active substances, such as enzymes, co-enzymes, enzyme inhibitors, hormones, antigens, antibodies, proteins, DNA, RNA etc., fixed on carriers such as cellulose, agarose, synthetic polymers, etc., are used in the separation, purification and transformation of other biochemically active substances. Properties required in such carriers include the following: (1) The carrier should be able to readily fix or immobilize a large quantity of a given biochemically active substance per unit weight of carrier; (2) The carrier should be biocompatible and sterilizable; (3) The carrier should have sufficient mechanical strength and stability so as to be capable of recycling many times with minimal loss of binding capacity; (4) The activity of the biochemically active substance while attached to the carrier should be good; (5) The materials which are held or entrapped by the biochemically active substance during use should be easily removable in order to permit ready availability of the biochemically active substance for re-use; and (6) The carrier, while possessing the foregoing properties, should be in a form which permits high flow rate of the fluids to be treated at low pressure drop. In the case of conventional carriers used to immobilize biochemically active substances, the aforementioned requirements are not adequately satisfied.

Polyimides have found extensive use in the electronics arena where they have proven useful in forming dielectric films as protective coatings on electronic and electrical devices, i.e. semiconductors, high temperature solder masks and bonding multilayer circuits. It is known in the polymer art to make all-aromatic polyimides by the condensation polymerization of dianhydrides and diamines to form polyamic acids which are then dehydrated to the polyimides (Edwards U.S. Pat. No. 3,179,634). Fryd U.S. Pat. No. 4,588,804 discloses polyimide compositions soluble in aprotic solvents. Gesslaer DE patent 3,523,615 discloses the use of polyimide coated materials, the surface of which are coated with gamma globulin. Wynberg WO patent 86/03840 discloses the use of polyimides (made from pyromellitic acid and bis(4-aminophenyl) oxide as immunoreagent carriers in thermochemiluminescence immunoassays.

SUMMARY OF THE INVENTION

Figure 1:
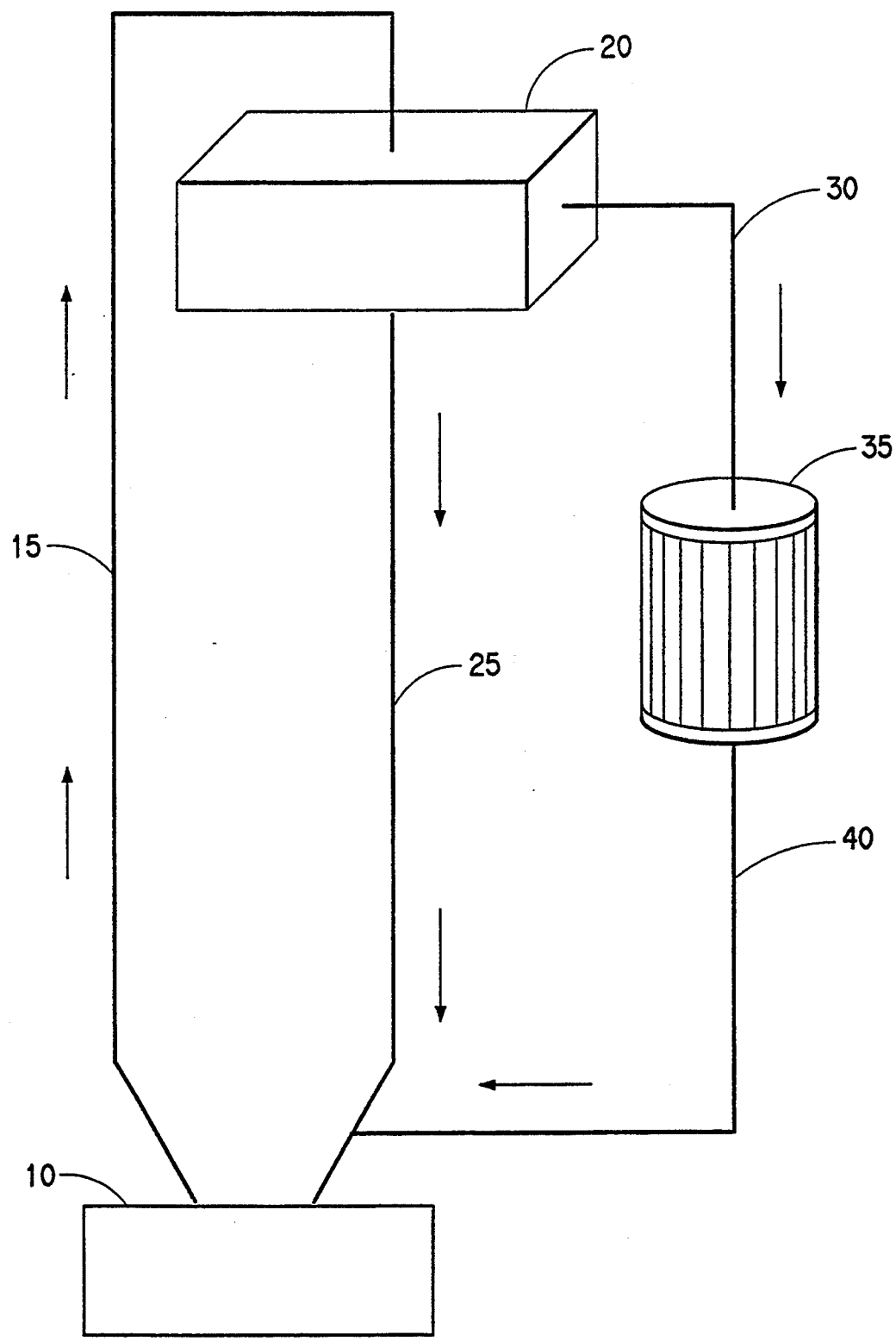
FIG. 1 is a schematic of a depletion column for extracorporeal treatment of body fluids.

The present invention is directed to the preparation of a particulate carrier, on which a treating agent can be immobilized, comprising mixing a solution of a polyimide in a solvent with a liquid coagulating medium and collecting the precipitated particulate carrier.

Further provided by this invention is a polyimide particulate carrier on which a treating agent can be immobilized having a surface area between about 5 and 600 $m^2$/gm with at least 50% by weight of the particles being between 50 and 500 microns in their longest dimension.

In another aspect of this invention, there is provided a process for immobilizing a treating agent comprising contacting the treating agent with the carrier of this invention in an aqueous solution at a pH in the range from 5 to 9.5. Also provided by this invention is the particulate carrier with a treating agent immobilized thereon.

Another aspect of this invention, is a process for removing a biochemically active substance from a fluid by contacting the fluid with the carrier of this invention with a treating agent immobilized thereon.

Another aspect of this invention is a process for filling a column with a carrier by the steps of evacuating air from the column, filling the column with a buffer and pouring a mixture of carrier and buffer into the buffer filled column, the improvement wherein the column is vibrated while introducing a stream of buffer into the column simultaneously with the mixture to agitate the particles.

DETAILED DESCRIPTION OF THE INVENTION

An important use for biochemically active substances is in the extracorporeal treatment of body fluids to separate, remove or otherwise modify other biochemically active substances present therein. This treatment involves withdrawal of the body fluid from the patient. The body fluid is contacted with a biochemically active substance to cause reaction, i.e. complexing, between the component of the body fluid sought to be removed and then the treated body fluid is returned to the patient. The biochemically active substance used to remove or modify other biochemically active substances is hereinafter referred to as a "treating agent". This operation is generally conducted in a continuous manner over a period of time. The treating agent complexed with the biochemically active substance can then be washed to remove the biochemically active substance to regenerate the treating agent for further use.

It is conventional in the art to support the treating agent on a carrier, several types of which have been previously known, in order to achieve efficient use of the treating agent. The carrier must be capable of immobilizing the treating agent without undue diminution of its activity, i.e. capacity to complex with a biochemically active substance. After usage, the treating agent must be capable of ready regeneration and re-use with little loss in capacity to complex with a biochemically active substance. During use, the filtration characteristics must be such as to permit high flow through rates at low pressure drop so that patient treatment time can be kept to a minimum.

There is provided by this invention a polyimide particulate carrier on which treating agents can be immobilized. The carrier has a surface area of from about 5 to 600 $m^2$/gm, at least 50% by weight of the particles being between 50 and 500 microns in their longest dimension. The carrier of this invention is gamma-ray sterilizable and hemocompatible.

The term "polyimide" as used herein is intended to include any isoimides that may be formed as a side reaction in the thermal or chemical imidization of a polyamide acid to the corresponding polyimide. One class of polyimides suitable for purposes of the present invention is described in U.S. Pat. No. 4,588,804 to Fryd which patent is hereby incorporated by reference.

In accordance with the present invention, one method of obtaining such a carrier is by mixing a polyimide solution with a liquid coagulating medium to cause coagulation of the polyimide and its precipitation as fibrid particles. A description of the term "fibrid" can be found in Morgan, U.S. Pat. No. 2,999,788 which is incorporated by reference. The polyimide solution comprises any polyimide dissolved in a suitable solvent. Conveniently, solutions having polyimide concentrations between about 5 and 30% by weight are useful.

Examples of suitable solvent media for the formation of the polyimide solution include N-methylpyrrolidone, dimethylacetamide, dimethylsulfoxide, dimethylformamide and metacresol.

The polyimide solution is mixed vigorously with the liquid coagulating medium, preferably by use of a Waring blender or other mixer providing good agitation. Any of a variety of coagulating media may be used; however, it has been noted that the surface area and the effectiveness of the carrier to immobilize the treating agent will vary with different coagulants. Examples of suitable coagulating media include methanol, water, dimethylsulfoxide or mixtures thereof. The resulting product is a fibrid particulate having a surface area of from about 5 to 600 $m^2/gm$, at least 50% by weight of the particles being between 50 and 500 microns in their longest dimension.

The carrier provided by the present invention can be used for immobilizing various treating agents such as proteins, antibodies or enzymes such as amylase, trypsin, chymotrypsin, aminoacylase, galactosidase, invertase, pectinase, L-asparaginase, glucose oxidase, urease and cellulase, etc. Such immobilized treating agents can be used for example, as reaction catalysts in the food industry, pharmaceutical industry or in clinical testing, or as adsorbing materials for the separation and purification of biochemically active substances in a fluid, for example, blood plasma.

The fixing or immobilizing of a treating agent on the carrier, can be achieved in one step by mixing together the treating agent, such as Protein A, and the particulate carrier of this invention in an aqueous solution at a pH in the range from 5 to 9.5. It is believed that the immobilization of a treating agent on the particulate carrier is accomplished by either a covalent bonding mechanism or a combination of polar and non-polar bonding mechanisms.

The polyimide particles bearing an immobilized treating agent of this invention can be used to remove a biochemically active substance from a fluid by contacting the fluid with the carrier of this invention bearing a suitable treating agent. Conveniently, the carrier with the treating agent immobilized thereon can be packed in a column and the fluid with the biologically active substance to be treated is passed through the column.

Applicants have discovered a process to pack the carrier of the present invention, with or without a treating agent immobilized thereon, in a column so as to achieve a column with flow characteristics exhibiting a low pressure drop and plug flow. The term "column" as used herein, is intended to include any suitable confining means for the particulate carrier of this invention. The column packed by the process of this invention is useful in a process for removing or modifying a biochemically active substance in a fluid such as blood plasma.

There is provided by this invention a process for filling a column with a carrier by the steps of evacuating air from the column, filling the column with a buffer and pouring a mixture of carrier and buffer into the buffer filled column, the improvement wherein the column is vibrated while introducing a stream of buffer into the column simultaneously with the mixture. Buffer displaced by the particles flows smoothly from the column.

In the improved process of this invention, a stream of buffer is introduced into the column simultaneously with the particulate-buffer mixture to impart additional motion to the particles to aid in optimum positioning of the particles as they begin to pack. The column is vibrated in order to impart vibration to the particles so that they move and seek the most efficient packing while displacing liquid. A reasonable combination of frequency and amplitude are selected depending on particle shape and size and column selection. Frequencies of less than 5000 Hz have been demonstrated.

Columns packed in this manner exhibit excellent flow performance useful for treating a variety of liquids, e.g. blood plasma. A column packed by the process of this invention has a pressure drop of less than 250 mm Hg and a Peclet number of less than 0.01.

The process of this invention for treating blood involves first removing blood from a patient and separating the blood into plasma and cellular components. The plasma component is passed through a column containing a polyimide particulate carrier. The polyimide carrier contains proteins, such as protein A, bonded to its surface. The polyimide carrier can be used for removing or modifying a biochemically active substance in the blood plasma. The treated plasma component and cellular component are then returned to the patient.

A simplified set-up for the extracorporeal treatment of a bodily fluid is shown schematically in FIG. 1. Shown in the figure is an inlet line 15 for introduction of a fluid substance to be treated, such as blood from a patient 10. Blood flows through the inlet line 15 to a plasma separator 20. The cellular component of the blood is returned to the patient through a line 25 and plasma to be treated exits through a line 30 leading to a column 35. The plasma flows through the body of the column 35 housing the carrier of the invention bearing a suitable immobilized treating agent. Following passage through the column 35, treated plasma exits through a line 40 and is returned to the patient 10. Flow rate and pressure build-up are measured with appropriately situated gauges, as the fluid to be treated passes through the column. A pressure drop across the column should be less than 250 mm Hg and preferably less than 100 mm Hg for acceptable operation.

TEST PROCEDURES

Surface Area Measurement

The surface area of hard polymers is determined by the Brunsuer, Emmet, and Teller (BET) method. The BET method is based upon the adsorption of unimolecular layer of a gas ($N_2$) upon the surface of the sample while the sample is maintained at a temperature close to the condensation temperature of the gas (77° K.).

The bulb containing the evacuated sample is immersed in liquid $N_2$ and a measured amount of $N_2$ gas is brought into contact with the samples. The amount adsorbed at each of a series of increasing pressures is determined. From these data, the volume of adsorbed gas corresponding to the formation of a unimolecular layer of $N_2$ on the sample can be deduced, and from the known molecular area of nitrogen, the specific area of the sample is calculated.

Reference: S. J. Gregg and K. S. W. Sing, Adsorption, Surface Area and Porosity, Second Edition, Academic Press, New York 1982, p. 42

Determining Protein Concentration

Lowry Protein assay using absorption at 750 nm and a UV absorption method at 280 nm are two of the most widely used methods for determining protein concentration. To determine protein concentrations for unknowns, a calibration curve for each protein was used. All absorptions described herein were determined with a Milton Roy Co., King of Prussia, PA Spectronic 1201 UV/visible spectrophotometer with an auto-sipper.

The Lowry protein assay used is commercially available in kit form from Sigma Chemical Co., St. Louis, MO (Kit P-5656). The Lowry assay was run directly on the soluble portion of unknown protein solutions.

Bovine Serum Albumin (BSA) and Protein A concentration calibration curves overlap at 750 nm. In analyses of Protein A, a BSA calibration curve was used whenever protein A concentrations needed to be determined.

The calibration curve for Protein A was determined by appropriately diluting BSA supplied in the Lowry kit with water as directed. Absorbencies were measured at 750 nm after the appropriate waiting time to verify concentrations. Water was used to clear the cell between each determination. The data were plotted and the unknown protein concentrations determined from this concentration curve.

A calibration curve for human IgG (CAPPEL-organon Teknika Corp., Malvern, Pa.) was determined in the same way as that for BSA. That is, IgG concentrations were prepared as discussed above for the Lowry determination of BSA and a calibration curve was determined by UV absorbance at 280 nm as well as absorbance at 750 nm.

Binding Ratio Calculated

Binding Ratio as used herein is the weight of IgG eluted (when the Protein A-IgG complex was disrupted with a citrate buffer wash as described in the Examples below) divided by the weight of Protein A immobilized.

The following examples are illustrative of the present invention. All percentages are by weight unless otherwise indicated.

EXAMPLE 1

Carrier Preparation

A soluble polyimide was prepared according to the general procedures described in M. Fryd, U.S. Pat. No. 4,588,804, issued May 1986. More specifically, the soluble polyimide of this Example was made via the polyamide-acid solution made according to the following procedure:

Polyamide-acid Formation

The polyamide-acid was prepared by slowly adding 2,2-bis(3,4-benzenedicarboxylic acid anhydride) perfluoropropane to a solution of 4,4'-sulfonedianiline and 4,4'-oxydianiline in N-methylpyrrolidone (NMP). All chemical reactants were combined in stoichiometric proportions, using a 50/50 mole% mixture of the reactive diamines. The solution was stirred at room temperature for 2 hours to form the polyamide-acid.

Thermal Imidization of Polyamide-acid

Xylene was added and the reaction solution heated to 180° C. for 4 hours to imidize the polymer and remove water. The reacted solution containing 20% by weight soluble polyimide in NMP was cooled to room temperature.

Preparation of Carrier

High surface area particulate carrier was obtained by slowly adding 200 ml of a diluted 10% by weight solution of the soluble polyimide prepared as above in N-methylpyrrolidone to 750 ml of coagulant (methanol) in a Waring blender over a 2-minute period. The coagulated particles were filtered and then washed two to three times with about 750 ml of methanol, and then three times with about 750 ml of distilled water in the blender. The particles were isolated and dried at 90° C. in a vacuum oven overnight. The dried particles were ground in a mortar to break up any agglomerations. The surface area as measured by nitrogen adsorption was about 110 $m^2/g$. Particle size was not determined, but at least 50% by weight were estimated to be between 50 and 500 microns in their longest dimension.

Protein A Immobilization

The immobilization of a treating agent, Protein A (Recombinant, E.coli, from CALBIOCHEM brand Biochemicals, San Diego, Calif.) to the carrier was determined by the measurement of the disappearance of Protein A from the solution in contact with the carrier. The amount of Protein A immobilized is the difference between the starting and final concentration of Protein A in solution as determined by the Lowry protein assay BSA Calibration curve described herein.

0.53 gram of the polyimide particles (dry weight) prepared above were added to a tared 15 mm internal diameter by 10 cm long Rainin column. The particles were washed very well to remove any soluble surface contaminants which might elute and interfere with the subsequent protein analyses. The particles were first washed with about 30 ml of methanol, then 30 ml of 0.1M citrate buffer (pH=2.3), then with 30 ml of distilled water and finally with 30 ml of 0.1M phosphate buffer (pH=8.3). The excess phosphate buffer was drained from the column and the weight of the damp particles determined. The weight of the retained phosphate buffer was used to calculate its dilution effect on the added Protein A solution.

A weighed amount of Protein A solution (about 12.9 g) of known concentration (about 5 mg/ml) in the phosphate buffer was added to the damp polyimide particles. The mixture was gently rolled for 24 hours at room temperature. Duplicate aliquots were removed from the mixture at 24 hours for Lowry protein analysis.

The Protein A containing particles were washed six times with 5 ml of phosphate buffer, then six times with 5 ml of citrate buffer. These washings were done to elute any Protein A which might elute later under the acid conditions used in the determination of Protein A activity described below. Lowry protein assays were run on all these fractions to account for all the Protein A. Lowry analyses showed that approximately 44 mg of Protein A were immobilized, i.e. 83 mg of Protein A were immobilized per gram of carrier after 24 hr.

Finally the particles were washed six times with 5 ml of phosphate buffered saline (PBS) pH=7.1. The excess PBS was drained from the column and the weight of the damp solids was re-determined. The weight of retained PBS was used to calculate its dilution effect on the added IgG solution in the determination of Protein A activity described below.

Protein A Activity

A weighed amount of human immunoglobulin (IgG) (CAPPEL-Organon Teknika Corp., Malvern, Pa.) solution (14.2 g) of known concentration (about 5 mg/ml) in PBS was added to the damp carrier with Protein A immobilized thereon. The mixture was rolled for 3 hours at room temperature. Duplicate aliquots were removed at 3 hours for Lowry and UV protein analyses to determine IgG concentration. The carrier containing the Protein A-IgG complex was washed six times with 5 ml each of PBS buffer to remove any free IgG. Lowry and UV analyses were determined on all these fractions to account for all the IgG. Approximately 63 mg of IgG was complexed, i.e. 119 mg of IgG was complexed per gram of carrier after 3 hours.

The Protein A-IgG carrier complex was then disrupted by lowering the pH of the wash buffer to 2.3 with citrate buffer. Six fractions, each 5 ml, were collected and analyzed by Lowry and UV analyses. Approximately 56 mg of IgG were eluted. The Binding Ratio of Protein A was calculated to be about 1.2.

Protein A Re-Use

The Protein A-carrier was then washed six times with 5 ml of PBS. This was to bring the pH back to 7.1 and reactivate the Protein A-carrier for additional IgG complexation reaction as described above.

The results are detailed below.

|  | IgG Eluted | Binding Ratio |
| --- | --- | --- |
| First Re-Use | 45 mg | 1.0 |
| Second Re-Use | 46 mg | 1.0 |

EXAMPLE 2

Carrier Preparation

High surface area particulate carrier was prepared by adding, at a controlled flow rate of 36 ml/min, 60 ml of a 10 weight percent solution of the polyimide prepared as described in Example 1 in N-methylpyrrolidone to a standard 1 liter Waring blender containing 600 ml of coagulant (methanol). This is a ratio of 1 to 10, respectively. The blender speed was set at 20, the lowest speed that created a vortex in the coagulant. The particles produced were filtered and washed three times with 4 liters of coagulant (methanol) and then with water. The particles were then washed extensively through a tier of successively smaller screen sizes (USA Standard Testing Sieve STME-11 Specification, C. E. Tylo, Inc., Mexico) with a Jet of tap water flowing through a 2 mm diameter nozzle. As the larger screen was thoroughly filtered, it was removed and the water stream was directed to the next smaller screen. This was continued until all the particles had been thoroughly screened.

This particle selection method gave the following particle size distribution (excluding fines) based on volume percent of the settled particles: >500 $\mu$m (25%), 300–500 $\mu$m (25%), 150–300 $\mu$m (25%), 106–150 $\mu$m (12%), and 38–106 $\mu$m (12%). Fines are estimated to be less than 10% by weight.

Protein A Immobilization

Approximately 0.3 g of the polyimide particles (dry weight) with a further selected size distribution of 300–400 $\mu$m and having a surface area of 58.3 m$^2$/g were added to a column and washed and the procedure of Example 1 for Protein A immobilization was followed.

Lowry analyses showed that approximately 15.6 mg, i.e. 52 mg of Protein A per gram of carrier were immobilized after 24 hours.

Protein A Activity

A weighed amount of human immunoglobulin was added to the damp immobilized Protein A-carrier and Protein A activity was determined as described in the procedure of Example 1. Approximately 43 mg of IgG (142 mg/g carrier) were complexed after 3 hours.

Approximately 37 mg of IgG were eluted (124 mg/g carrier) after the washing. The Binding Ratio efficiency of Protein A was calculated to be about 2.4.

Protein A Re-Use

The Protein-A carrier was then washed with 30 ml of PBS. This brought the pH back to 7.1 and reactivated the Protein A-carrier for another IgG complexation reaction.

|  | IgG Eluted | Binding Ratio |
| --- | --- | --- |
| Re-Use | 42 mg (140 mg/g) | 2.7 |

EXAMPLE 3

Carrier Preparation Continuous Carrier Production Method

A 2 liter Waring blender was modified with an inlet port at the bottom and an overflow port at the top and filled with 1.4 liters of a 20% dimethylsulfoxide (DMSO)-water coagulant solution. The 10% polyimide solution described in Example 1 was added to the rapidly stirred coagulant at 70 ml/min while fresh DMSO solution was being pumped continuously into the bottom port of the blender at a flow rate of 108 ml/min. The temperature of the contents in the blender were maintained at approximately 50° C. by a water-cooled coil wrapped around the blender.

The particles produced exited the top of the blender and dropped into 4 liters of 20% DMSO in water and gently stirred with an air stirrer. The particles were filtered and washed three times for 30 minutes with 6 liters of methanol and then with water. The particles were classified into various particle sizes through a tier of screens as described in Example 2. The following particle size distribution (excluding fines) was obtained: >300 $\mu$m (28%), 150–300 $\mu$m (33%), 106–150 $\mu$m (16%), 53–106 $\mu$m (23%).

Although this is a continuous process method, production of carrier was terminated after 3 hours. Approximately 1.2 kg of particulate carrier was produced.

Protein A Immobilization

Approximately one gram of the polyimide particles (dry weight) with sizes ranging from 106–150 $\mu$m, with a surface area of about 5 m$^2$/g prepared as described above were added to a column and washed and the procedure of Example 1 was followed.

Lowry analyses showed that approximately 9.4 mg of protein A were immobilized after 24 hours.

Protein A Activity

A weighed amount of human immunoglobulin (IgG) was added to the damp immobilized Protein A-carrier and Protein A activity was determined as described in the procedure Example 1. Approximately 28 mg of IgG was complexed with Protein A after 3 hours.

Approximately 28 mg of IgG were eluted after washing as described in Example 1. The Binding Ratio of Protein A was calculated to be about 2.9.

Protein A Re-use

The Protein A-carrier was then washed with 30 ml of PBS. This brought the pH back to 7.1 and reactivated the Protein A-carrier for another IgG complexation reaction.

|        | IgG Eluted | Binding Ratio |
|--------|------------|---------------|
| Re-use | 26 mg      | 2.7           |

EXAMPLE 4

A polycarbonate column, 4 cm in diameter×5 cm height (62 ml volume), was fastened to a clamp mounted on a vibrating head. The vibrating head was controlled by a variable frequency excitation source. The column was mounted on its side with an inlet port (a tube $\frac{3}{8}$" I.D.×$\frac{1}{2}$" O.D. extending $\frac{1}{2}$" from the center of the column) facing up. The column was fitted at the top and the bottom with three-way stopcocks. One stopcock was attached to a length of tubing connected to a one liter plastic bag filled with PBS and was in the off position.

The other stopcock was connected to a length of vacuum tubing attached to a 2 liter vacuum flask, which, in turn was connected by means of another length of tubing to a standard laboratory vacuum pump. A section of silicone tubing, 1$\frac{1}{2}$" long, $\frac{3}{8}$" diameter was placed over the inlet port and was clamped off with a hemostat. The stopcock to the vacuum line was open.

The vacuum pump was run for 10 minutes, creating a vacuum equal to 0.1 mm Hg. Then, a clamp was placed on the vacuum line between the column and the vacuum flask, close to the flask, leaving the column under vacuum. The stopcock to the Phosphate Buffered Saline line was opened and the liquid filled the column, keeping the column devoid of air. When the column was completely filled with PBS, both stopcocks were shut off. The vacuum line and the line to the buffer were removed from the column, and in their place, a length of tubing 30" long was connected to each stopcock.

Then, with the liquid filled column still isolated, a glass funnel, 5$\frac{1}{2}$" diameter with a stem $\frac{3}{4}$" long was attached to the silicone tubing on the inlet port, and mounted directly over the inlet port, held in place by a ring clamp. The clamp on this silicone tubing was removed. The vibrating head was turned on and the column was continuously vibrated at a frequency of 100 Hz. A stainless steel tube, 10" long with a 1/16" diameter hole was placed into the funnel, extending into the inlet port to a point $\frac{1}{8}$" above the mouth of the column. The stainless steel tube was connected to a container of PBS which was pumped into the column through the stainless steel tubing at a flow rate of 70 ml/minute.

Adjacent to this apparatus was a beaker containing a slurry of carrier dispersed by means of a magnetic stirrer. The slurry was made up of 20 g of carrier prepared as described in Example 3 and approximately 400 ml of PBS.

As the flow into the column from the stainless steel tubing continued, the level of liquid in the funnel began to rise. When the level of the liquid reached 1$\frac{1}{2}$' from the top, the addition of the carrier slurry began. A 30 ml aliquot of the carrier slurry was added to the funnel reservoir. At this point, the stopcocks on either end of the column were opened and liquid began flowing from the vibrating column and was displaced by the carrier slurry. As the carrier entered through the fill port, the particles were in a state of swirling flux because of the flow from the stainless steel tubing and the vibrating column. They deposited themselves at each end of the column, continuously filling towards the center as additional carrier was added to the reservoir. A level of liquid slurry was maintained in the reservoir throughout the filling cycle, preventing any air from entering the column. Carrier was added to the reservoir until the column was filled. Then, the stopcocks were closed off, the stainless steel tubing removed, the vibrating device shut off, and the funnel reservoir was removed from the column. A plug was placed in the inlet port and sealed in place. This fill cycle was completed in about 30 minutes.

A flow-through conductivity probe (Lazar Research Laboratories, Inc., Los Angeles, Calif.) and a pressure transducer (Omega Engineering Inc., Stamford, Conn.) were mounted at the inlet and at the outlet of the filled column. Distilled water was pumped through the column at 30 ml/min. A 1 ml portion of a 1% NaCl solution was injected above the inlet of the column and before the conductivity probe and pressure transducer. The inlet probe detects and records the conductive pulse generated by the NaCl solution. The exit probe detects and measures the conductivity-time distribution curve generated by a NaCl solution as it exits the column. From the shape of the curve, the quality of the packing is determined.

Plug flow can be determined by the Peclet number. The Peeler number ($P_e$) is defined by the following formula:

$$P_e = \frac{D}{uL}$$

wherein:
  D is the dispersion coefficient
  u is the average linear velocity of the fluid
  L is the length of the column $P_e$ can be calculated from a Gaussian distribution curve using the following formula (Chemical Reaction Engineering, 2nd Edition (1972):

$$2P_e = (\sigma/t)^2$$

where "$\sigma$" is the standard deviation and "t" is the average residence time of the sodium chloride ions in the column. A Peclet number of 0.006±0.002 was determined.

Pressure drop across the column is determined by the difference in pressures measured by the inlet and outlet pressure transducers in mm of Hg. The pressure drop was 50 mm Hg±25.

We claim:

1. A process for treating blood, comprising the following steps:
   a) removing blood from a patient;
   b) separating the removed blood into a plasma component and a cellular component;
   c) passing the plasma component through a column containing polyimide particulate carriers having proteins bonded to their surfaces, wherein the polyimide carriers are soluble in aprotic solvents and have a surface area between about 5 and 600 $m^2/gm$ with at least 50% by weight of the particles being between about 50 and 500 microns in their longest dimension; and
   d) returning the treated plasma component and cellular component to the patient.

2. The process of claim 1, wherein the proteins bonded to the surfaces of the carriers are Protein A.

3. The process of claim 1, wherein the pressure drop across the column as the plasma component passes through the column is less than 250 mm Hg.

* * * * *